US006469186B1

(12) United States Patent
Kasitu et al.

(10) Patent No.: US 6,469,186 B1
(45) Date of Patent: Oct. 22, 2002

(54) PROCESS FOR MASS PRODUCTION OF GMP PACLITAXEL AND RELATED TAXANES

(75) Inventors: Gertrude C. Kasitu; Japheth Noah, both of New Mina; Qasim Khan, Coldbrook, all of (CA)

(73) Assignee: Actipharm, Inc., halifax (CA)

( * ) Notice: Subject to any disclaimer, the term of this patent is extended or adjusted under 35 U.S.C. 154(b) by 0 days.

(21) Appl. No.: 10/007,567

(22) Filed: Nov. 7, 2001

Related U.S. Application Data
(60) Provisional application No. 60/246,850, filed on Nov. 8, 2000.

(51) Int. Cl.$^7$ .............................................. C07D 305/14
(52) U.S. Cl. ...................................... 549/510; 549/511
(58) Field of Search ................................ 549/510, 511

(56) References Cited

U.S. PATENT DOCUMENTS

| | | | |
|---|---|---|---|
| 5,279,949 A | 1/1994 | Nair | 435/123 |
| 5,336,684 A | 8/1994 | Murray et al. | 514/449 |
| 5,380,916 A | 1/1995 | Rao | 560/107 |
| 5,475,120 A | 12/1995 | Rao | 549/510 |
| 5,478,736 A | 12/1995 | Nair | 435/123 |
| 5,480,639 A | 1/1996 | ElSohly et al. | 424/195.1 |
| 5,530,020 A | 6/1996 | Gunawardana et al. | 514/449 |
| 5,618,538 A | 4/1997 | ElSholy et al. | 424/195.1 |
| 5,654,448 A | 8/1997 | Pandey et al. | 549/510 |
| 5,670,673 A | 9/1997 | Rao | 549/510 |
| 5,965,752 A | 10/1999 | Zamir et al. | 549/510 |
| 5,969,165 A | 10/1999 | Liu | 549/510 |
| 6,061,929 A | 5/2000 | Pare et al. | 34/423 |
| 6,136,989 A | 10/2000 | Foo et al. | 549/510 |
| 6,229,027 B1 | 5/2001 | Liu | 549/510 |

FOREIGN PATENT DOCUMENTS

WO WO 01/51476 7/2001

OTHER PUBLICATIONS

International Search Report.
Yu, Guang'ao et al., "Research on different solvent extractin of taxol form Taxus cell", Chemical Abstracts, vol. 134, No. 18, p. 570, 2000.
Ketchum, Raymond E.B. et al., "Efficient extraction of paclitaxel and related taxoids from leaf tissue of Taxus using a potable solvent system", Chemical Abstracts, vol. 131, No. 12, 1999.
Pandey et al., "Synthesis and Separation of Potential Anticancer Active Dihalocephalomannine Diastereomers from Extracts of Taxus yunnanensis", *Journal of Natural Products*, vol. 61, No. 1, 1998, pp. 57–63.
Cragg et al., "Natural Products in Drug Discovery and Development", *Journal of Natural Products*, vol. 60, No. 1, 1997, pp. 52–60.

Beckvermit et al., "An Improved Method for Separating Paclitaxel and Cephalomannine Using Ozone and Girard Reagents", *J. Org. Chem.*, vol. 61, No. 25, 1996, pp. 9038–9040.
Nicolaou et al., "Total Synthesis of Taxol", *Letters to Nature*, vol. 367, 1994, pp. 630–634.
Gunawardana et al., "Isolation of 9–Dihydro–13–Acetylbaccatin III From Taxus Canadensis", *Journal of Natural Products*, vol. 55, No. 11, 1992, pp. 1686–1689.
Kingston et al., "Modified Taxols, $7^1$ A Method for the Separation of Taxol and Cephalomannine", *Journal of Natural Products*, vol. 55, No. 2, 1992, pp. 259–261.
Witherup et al., "Taxus SPP. Needles Contain Amounts of Taxol Comparable to the Bark of Taxus Brevifolia: Analysis and Isolation", *Journal of Natural Products*, vol. 53, No. 5, 1990, pp. 1249–1255.
Schiff et al., "Promotion of microtubule assembly in vitro by taxol", *Nature*, vol. 277, 1979, pp. 665–667.
Wani et al., "The Isolation and Structure of Taxol, a Novel Antileukemic and Antitumor Agent from Taxus Brevifolia", *Journal of the American Chemical Society*, vol. 93:9, 1971, pp. 2325–2327.
Pan et al., "Microwave–assisted extraction of tanshinones from *Salvia miltiorrhiza* bunge with analysis by high–performance liquid chromatography", *Journal of Chromatography A*, 922, 2001, pp. 371–375.
Jones et al., "Comparison of Methods for Extractin of Tabacco Alkaloids", *Journal of AOAC International*, vol. 84, No. 2, 2001, pp. 309–316.
Guo et al., "Microwave–assisted extraction of effective constituents from a Chinese herbal medicine *Radix puerariae*", *Analytica Chimica ACTA*, 436, 2001, pp. 41–47.
Shotipruk et al., "Feasibility Study of Repeated Harvesting of Menthol from Biologically Viable Mentha x piperata Using Ultrasonic Extraction", *Biotechnol. Prog.*, vol. 17, No. 5, 2001.
Valachovic et al., "Towards the industrial production of medicinal tincture by ultrasound assisted extraction", *Ultrasonics Sonochemistry*, 8, 2001, pp. 111–117.
Eskilsson et al., "Analytical–scale microwave–assisted extraction", *Journal of Chromatography A*, 902, 2001, pp. 227–250.
Vila et al., "Optimization of an extraction method of aroma compounds in white wine using ultrasound", *Talanta*, 50, 1999, pp. 413–421.

(List continued on next page.)

Primary Examiner—Ba K. Trinh
(74) Attorney, Agent, or Firm—Dorsey & Whitney LLP; Scott D. Rothenberger

(57) ABSTRACT

A process for the purification of paclitaxel and/or cephalomannine and/or 10-DAB III and/or 9-DHAB III is described. A series of extractions, separations, and purifications provides these products in commercial quantities with high purity. The source for these natural products is from readily available renewable biomaterials, such as leaves and stems from the yew, *T. canadensis*.

25 Claims, 5 Drawing Sheets

OTHER PUBLICATIONS

Hromadkova et al., "Comparison of classical and ultrasound–assisted extraction of polysaccharides from *Salvia officinalis* L.", *Ultrasonics Sonochemistry*, 5, 1999, pp. 163–168.

Booth et al., "Polymer–Supported Quenching Reagents for Parallel Purification", *J. Am. Chem. Soc.*, vol. 119, No. 21, 1997, pp. 4882–4886.

Mattina et al., "Microwave–Assisted Extraction of Taxanes from Taxus Biomass", *J. Agric. Food Chem.*, vol. 45, No. 2, 1997, pp. 4691–4696.

Hui et al., "Isolation of polybutenylsuccinimide–type dispersant from monograde and multigrade lubricating oils by classical liquid–adsorption chromatography on a Florisil column", *Analytica Chimica Acta*, 314, 1995, pp. 161–167.

Rao, "Taxol and Related Taxanes. I. Taxanes of *Taxus brevifolia* Bark", *Pharmaceutical Research*, vol. 10, No. 4, 1993, pp. 521–524.

**Paclitaxel 1
(TAXOL)**

**Docetaxel 2
(TAXOTERE)**

Cephalomannine 3

9-Dihydro 13-acetylbaccatin III 4

R = Ac, Baccatin III 5
R = H, 10-DAB III 6

PROCESS FOR MASS PRODUCTION OF GMP PACLITAXEL AND RELATED TAXANES

CROSS-REFERENCE TO RELATED APPLICATION

This application is based on and claims priority to U.S. Provisional Application 60/246,850, filed on Nov. 8, 2000, entitled "Process for Mass Production of GMP Paclitaxel and Related Taxanes", the contents of which are incorporated herein by reference in their entirety.

BACKGROUND OF THE INVENTION

The search for new pharmacologically active agents by screening natural sources such as plant, microbial, and fermentation products has led to the discovery of many clinically useful drugs that play a major role in the treatment of human diseases. To date, close to 60% of anti-tumor and anti-infective agents available commercially, or in late stages of clinical trials, are of natural product origin.

In the 1960s, the National Cancer Institute initiated a program to screen large collections of compounds, natural or synthetic for anti-tumor activity. These activities lead to the discovery of one of the most significant compounds in the fight against cancer. An extract from a relatively rare Pacific yew (*Taxus brevifolia nutt.*) showed unique anti-tumor activity. The active principle, paclitaxel (Taxol™, 1) was isolated. Taxol™ is a registered trademark of Bristol-Myers Squibb. Paclitaxel binds to microtubules and inhibits their depolymerization into tubulin. Paclitaxel blocks the cell's ability to break down the mitotic spindle during mitosis. With the spindle still in place the cell cannot divide into daughter cells. In 1992 the FDA approved paclitaxel for refractory ovarian cancer. Today paclitaxel is used to treat a variety of cancers, including ovarian, breast, non-small lung, and Karposis sarcoma.

Natural paclitaxel was originally isolated from the bark of *Taxus brevifolia*. This species is slow growing, taking over a hundred years for a young yew to mature. More importantly, paclitaxel occurs in low concentrations, (0.002 to 0.04% per dry weight), primarily in the inner bark of the tree. Deforestation of this particular yew is an obvious concern and poses a problem for replenishing the naturally occurring limited supply of paclitaxel. Since the demand for paclitaxel increases every year, the scientific community has been forced to look for alternative ways of producing paclitaxel.

Alternative methods for the production of paclitaxel include the use of renewable plant parts, nursery production of yew trees, plant cell culture, semi synthesis from other natural taxane precursors, and total synthesis from simple starting materials.

To date, only semi synthetic approaches have found commercial utility. Taxol and Taxotere (2, a chemotherapeutic semi synthetic analog of paclitaxel) are produced commercially by semi synthesis from 10-deacetylbaccatin III (10-DAB III), a natural taxane isolated (0.02 to 0.1% per dry weight) from the needles of the English yew, *Taxus baccata*. Bristol-Myers Squibb, the sole supplier of paclitaxel in North America and a major world supplier, produces most of its paclitaxel semi synthetically. Nonetheless, this approach has not fulfilled the demand for paclitaxel.

Substantial effort has gone into the total synthesis of paclitaxel and paclitaxel analogs since its discovery three decades ago. To date, five elegant and unique routes to paclitaxel have been reported since the first successful synthetic report by Nicolaou. Because the paclitaxel molecule is structurally complex, the known synthetic processes are costly and have yields that hinder commercial viability.

In as much as plant cell culture has merit for producing a large-scale quantity of paclitaxel, this approach has yet to be scaled up to produce industrial scale quantities. Lengthy and complex cell culture procedures are involved.

The use of cultivable and renewable plant parts, such as the leaves (needles) and stems of Taxus species is currently the most practical and attractive way of increasing the supply of paclitaxel. The needles of several Taxus species, including *Taxus canadensis*, have been investigated and found to contain paclitaxel in amounts comparable to the bark of *Taxus brevifolia*.

*Taxus canadensis* is an evergreen shrub found in Eastern Canada and Northeastern United States. This species is unique in its taxane content. The needles contain a major taxane, 9-dihydro-13-acetylbaccatin III (9-DHAB III, 4) along with paclitaxel (0.009–0.05%), 10-deacetylbaccatin III (10-DAB III, 6), baccatin III, (5), cephalomannine, (3), and other minor taxanes. The concentration of 9-DHAB III in the needles is reportedly seven to ten times the concentration of paclitaxel. It already appears that 9-DHAB III may become an important precursor to a new class of semi-synthetic chemotherapeutic agents with increased water solubility.

Therefore, a need exists that provides commercial quantities of the above-referenced natural products from readily available renewable sources.

SUMMARY OF THE INVENTION

The process of the present invention is simple and cost effective. It provides paclitaxel and other taxanes in high yield and purity on industrial scale. The process of the present invention is more efficient since it provides 9-DHAB III in high yield and purity in a single chromatography step. Furthermore, paclitaxel, cephalomannine and 10-deacetylbaccatin III are obtained in high yield and purity in three chromatography steps, or at best two steps from the crude alcoholic extract without chemical transformation or destruction of any taxane.

The present invention provides methods for mass production of paclitaxel and related taxanes from plants of the genus Taxus (Taxaceae). More specifically, the present invention relates to a simple cost effective method for mass production of GMP paclitaxel, 9-dihydro 13-acetylbaccatin III, 10-deacetylbaccatin III, and cephalomannine from *Taxus canadensis*.

The present invention therefore, provides cost-effective processes for mass production of GMP paclitaxel and other related taxanes from a vegetal source or tissue culture particularly, *T. canadensis*.

The present invention also provides paclitaxel in high yield and purity. The present invention also produces industrial scale quantities of other taxanes namely, 9-DHAB III, 10-DAB III, and cephalomannine in high yield and purity.

BRIEF DESCRIPTION OF THE FIGURES

Other objects, advantages and features of the present invention will be readily appreciated as the same becomes better understood by reference to the following detailed description when considered in connection with the accompanying figures, in which like reference numerals designate like parts throughout the figures thereof and wherein.

DETAILED DESCRIPTION OF THE INVENTION

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

The present invention provides for the isolation of commercially important natural products from readily available biomass. More specifically, extraction procedures provided by the present invention afford the separation of natural products, e.g., paclitaxel, from naturally occurring sources. The invention provides steps with processes for such separation and purification.

Few isolation procedures for paclitaxel and other taxanes from bark, needles, or cell culture of Taxus species are currently amenable to industrial scale production.

Figure 1:
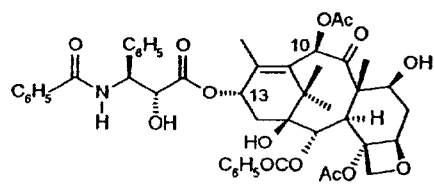
FIG. 1 depicts the formula for paclitaxel, docetaxel, cephalomannine, 9-dihydro-13-acetylbaccatin III, baccatin III, and 10-DAB III.
Figure 1:
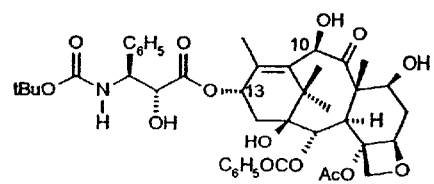
Figure 1:
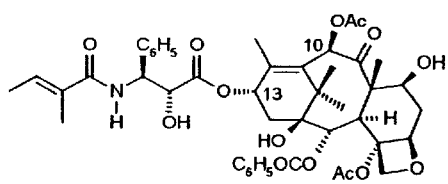
Figure 1:
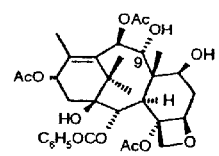
Figure 1:
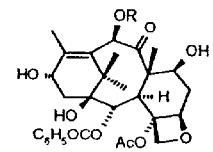

The current procedures are lengthy, costly, or are practically limited to analytical scale. Since paclitaxel occurs in low levels in needles and the needle contains large amounts of waxes, the isolation and purification of paclitaxel from needles to a clinically acceptable purity for FDA approval pose additional challenges. A daunting task is the separation of paclitaxel from its closely related analogue cephalomannine, (3) (See FIG. 1) which occurs in the needles and bark. The two analogues have been separated by selective chemical transformation of cephalomannine in a mixture containing both cephalomannine and paclitaxel. Disadvantages associated with these procedures include additional cost from use of expensive sometimes, toxic reagents, additional chromatography required to separate the transformed cephalomannine from paclitaxel, the destruction of cephalomannine and sometimes paclitaxel is during the process, and additional chemical transformations are necessary for recovery of cephalomannine.

In general, the methods of the invention begin with extraction of biomass with a lower alcohol including, but not limited to, methanol, ethanol, aqueous methanol or aqueous ethanol or combinations thereof providing a first crude alcoholic extract.

Figure 2:
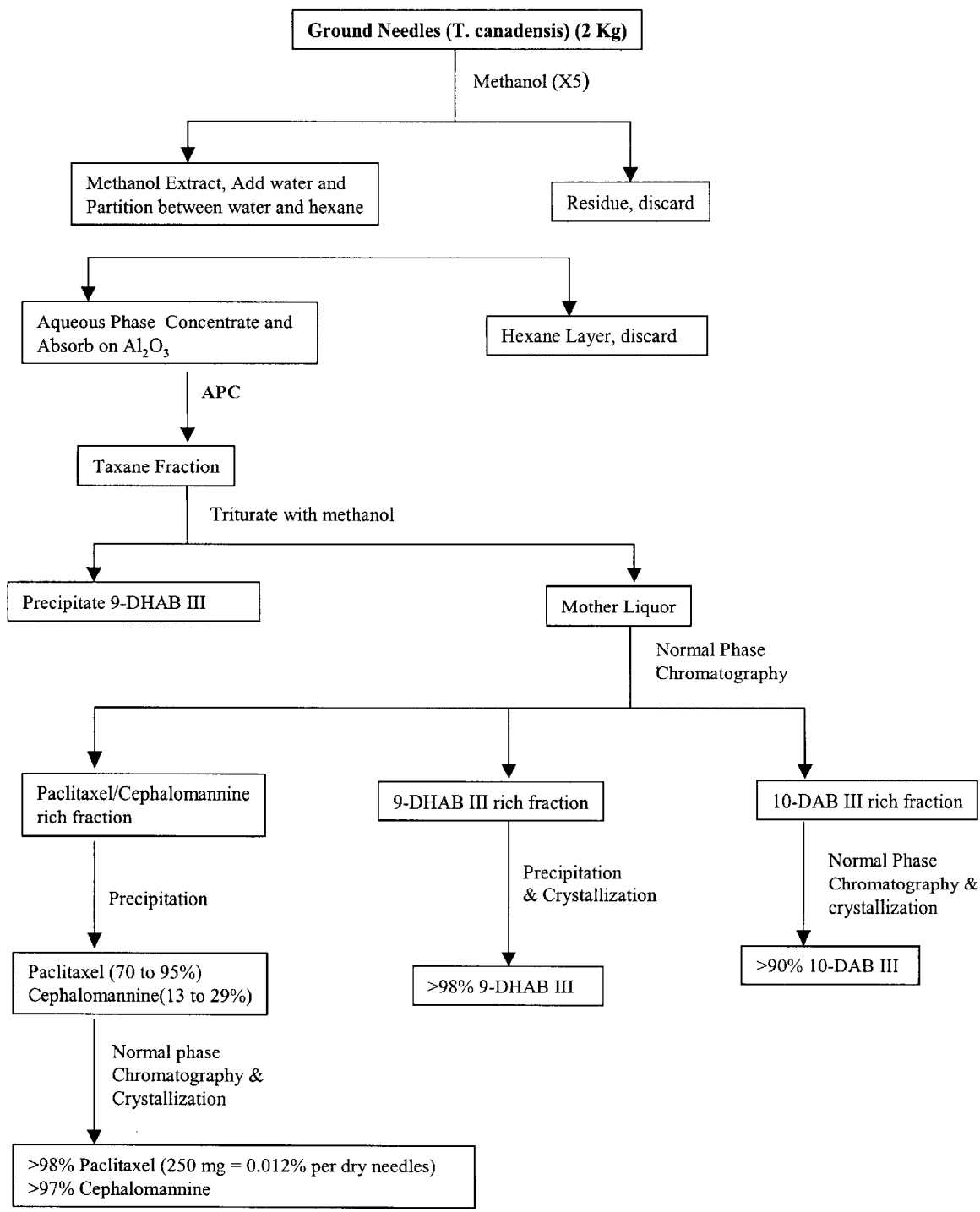
FIG. 2 is a flow diagram for the isolation and purification of paclitaxel, cephalomannine, 9-dihydro-13-acetylbaccatin III, and 10-DAB III.

The first crude alcoholic extract is concentrated under reduced pressure to obtain a viscous residue (See FIG. 2). The first viscous residue is de-fatted by distribution between aqueous alcohol and hexane, equilibration, and separation of the aqueous alcohol and hexane layers. The aqueous alcohol layer is concentrated under reduced pressure to obtain a first solid residue.

The first solid residue is re-dissolved in a minimum volume of suitable solvent and is then adsorbed onto a solid support, and air-dried to a free flowing powder. The free flowing powder is washed on a sintered funnel with dichloromethane or dichloromethane/ethyl acetate mixtures to remove less polar taxane or none taxane secondary metabolites, followed by washing with a mixture of dichloromethane and a second more polar organic solvent to obtain a second concentrated taxane residue. The second taxane residue is triturated with a suitable organic solvent to precipitate the first single taxane, 9-DHAB III (70 to 90% of total 9-DHAB III in the mixture). The precipitated 9-DHAB III is re-crystallized from a suitable organic solvent including but not limited to a acetone, acetone/hexane, tetrahydrofuran/hexane a lower alcohol such as methanol, ethanol, isopropyl alcohol or combinations thereof, to obtain 9-DHAB III of purity greater than 98%.

Chromatography of the mother liquors obtained from the previous step were developed on a normal phase adsorbent to afford three main taxane component fractions: A (paclitaxel/cephalomannine rich, B (9-DHAB III rich) and C (10-DAB III rich). Fraction B is processed according to the previous trituration and re-crystallization procedure (described above) to obtain more 9-DHAB III.

Fraction A is precipitated with a suitable organic solvent to obtain a solid residue containing paclitaxel and cephalomannine.

Chromatographic separation of the precipitated paclitaxel/cephalomannine solid residue on a suitable adsorbent, including but not limited to silica gel and aluminum trioxide, affords pure paclitaxel and pure cephalomannine fractions. These fractions are concentrated, separately, under reduced pressure to obtain solid residues. Re-crystallization of the paclitaxel and cephalomannine from a suitable solvent provides paclitaxel (>98%) and cephalomannine (>97%) of acceptable clinical purity.

Further chromatography of fraction C on a suitable adsorbent provides 10-DAB III of at least 70% in purity. Re-crystallization of the 10-DAB III from a suitable organic solvent affords 10-DAB III having a purity of >90%.

Extraction

The starting material for use in the present invention can be any vegetable material from the genus Taxus. The material can be any part of the plant, fresh or dried, containing taxanes, and includes the leaf, stem, twig, bark, root or mixtures thereof. A preferred source material according to one method of this invention, is dried ground needles and stems of Taxus species, more specifically, *T. canadensis*.

Cold Percolation

Ground dry material is soaked in a lower alcohol, such as methanol, ethanol, aqueous methanol, aqueous ethanol or combinations thereof, at between room temperature and 60° C., preferably at room temperature for about 24 hours. The weight to volume ratio of ground needles to alcohol is from about 1:7 to about 1:3, preferably 1:3. After the first 24 hour soak period, the solution is drained and the residue needles are re-soaked for 24 hours at least two more times during 48 hours. The combined alcoholic extracts are concentrated under reduced pressure to one twentieth the original volume to afford a viscous residue, the primary crude extract.

Microwave Extraction (ME)

In another method of this invention, ground fresh or dry material is contacted with a suitable solvent including but not limited to methanol, ethanol, isopropyl alcohol, acetonitrile, acetone, ethyl acetate, dichloromethane, or mixtures of. The weight to volume ratio of ground material to solvent is from about 1:3 to about 1:2, preferably 1:2. The mixture is agitated for 2 minutes by mechanical stirring and then exposed to microwave radiation for 20 seconds. The mixture is again agitated by mechanical stirring for a second 2 minute period and then exposed to microwave radiation for 20 seconds. The solution is drained and the residue solids are contacted with fresh solvent, and the two-cycle agitation for 2 minutes and exposure to microwave radiation for 20 seconds is repeated at least once more. The combined extracts are concentrated under reduced pressure and processed according to the methods of this invention.

Alternatively, the ME procedure is carried out in two stages. Accordingly, ground material is first contacted with hexane. The weight to volume ratio of ground material to hexane is from about 1:3 to about 1:2, preferably 1:2. The mixture is subjected to a two-cycle agitation for 2 minutes, microwave radiation exposure for 20 seconds, and draining. The residue is contacted with fresh hexane and the two-cycle agitation, microwave exposure, and draining is repeated at least once more. The residue solids are finally contacted with appropriate extraction media such as denatured alcohol and subjected to the ME procedure in a similar manner described above. The combined alcoholic extracts are concentrated under reduced pressure and are adsorbed directly onto a solid support or processed further by liquid-liquid partition between dichloromethane and water.

Ultrasound Assisted Extraction (USE)

In another method of this invention, fresh or dry ground material is contacted with suitable extraction media in a ratio of ground material to extraction media similar to the ME procedure. The mixture is subjected to ultrasound for a period of half to an hour with the temperature maintained between 20 and 30° C. The solution is drained, the residue solids are contacted with fresh extraction media, and subjected to ultrasound at least once more for half to an hour period. The combined crude extracts are concentrated under reduced pressure and processed according to procedures described below. The relatively short extraction time for USE allow for a similar de-fating step with hexane described above for the ME procedure.

ME and USE procedures have been shown to be more efficient and more economical compared to the cold percolation procedure. Solvent usage and extraction times are reduced. Fresh or dry needles are usable unlike in the cold percolation procedure where dry material is more preferred. The overall yield of extractable taxanes is increased especially when denatured alcohol and fresh needles are used in both ME and USE. An added advantage for the USE procedure is higher chromatographic purity or lower quantity of primary extract (crude alcoholic extract) obtained by this procedure compared to the extracts obtained by the cold percolation and ME procedures (Table 1a).

These extraction methods which utilize microwave and ultrasonic technology has never been applied to the production of pharmaceutically important natural products such as paclitaxel. The method presented in this invention are cost effective and highly efficient.

TABLE 1a

Comparative Extraction of *T. canandesis* needles

| Method of Extraction | USE | ME | Cold percolation |
| --- | --- | --- | --- |
| Weight of ground needles | 116.1 | 101.2 | 115.3 |
| Weight of Primary Ext. (g) | 37.0 | 48.3 | 46.0 |
| Weight of crude dichloromethane Ext. (g) | 5.9 | 5.5 | 5.6 |
| Recoverable paclitaxel (mg) | 47.1 | 46.7 | 48.6 |

TABLE 1a-continued

Comparative Extraction of *T. canandesis* needles

| Method of Extraction | USE | ME | Cold percolation |
| --- | --- | --- | --- |
| Recoverable 9-DHAB III (mg) | 92.4 | 92.0 | 93.7 |

Table 1a depicts data from comparative extraction methodologies of *T. canandesis* needles.

Scavenging of Taxanes

Liquid-Liquid Partition 1 (LLP1)

Figure 4:
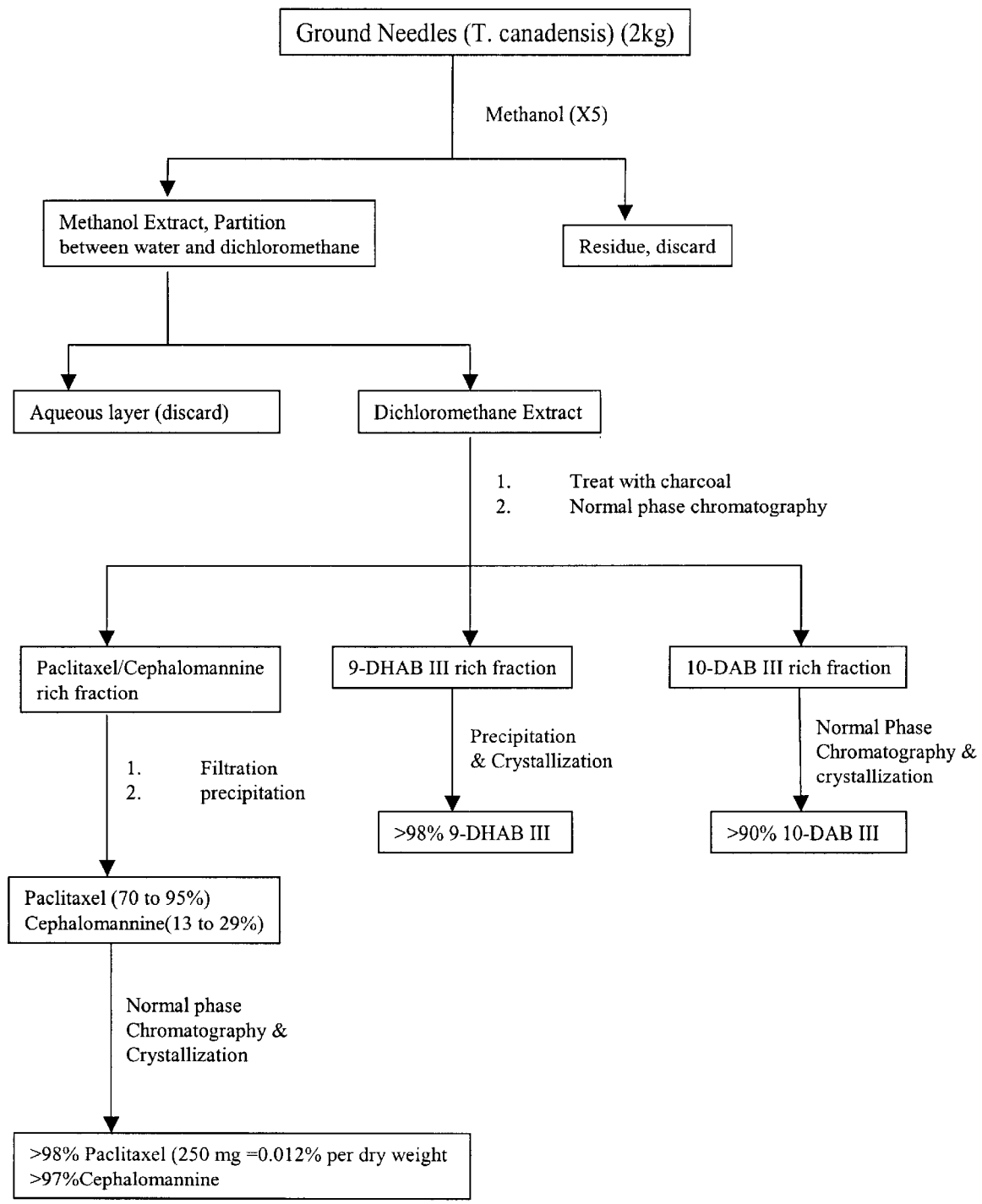
FIG. 4 is a flow diagram for the isolation and purification of paclitaxel, cephalomannine, 9-dihydro-13-acetylbaccatin III, and 10-DAB III.

In one embodiment (FIG. 4), the first viscous residue is diluted with aqueous methanol in about 1:1 to about 1:5, (v/v) ratio of water to methanol, preferably about 1:1. The resultant solution is extracted with a suitable organic solvent such as dichloromethane, chloroform, ethyl acetate, preferably dichloromethane in about 2:1 (v/v) ratio of dichloromethane to aqueous methanol. The solution is well mixed, and the layers are separated (when two distinct layers are observed). The aqueous layer is extracted once more with dichloromethane. The combined dichloromethane layers are treated with activated charcoal (about 10–15% w/w of original biomass) and agitated for about 10–15 minutes at room temperature. The solution is filtered over celite and the filtrate is concentrated under reduced pressure to obtain a second residue containing taxanes. It has been surprisingly discovered that the activated charcoal is more effective in removing chlorophylls and lipids at this stage of the process rather than adding the charcoal to the first alcoholic extract as taught in other earlier procedures.

Liquid-Liquid Partition 2 (LLP2)

Figure 5:
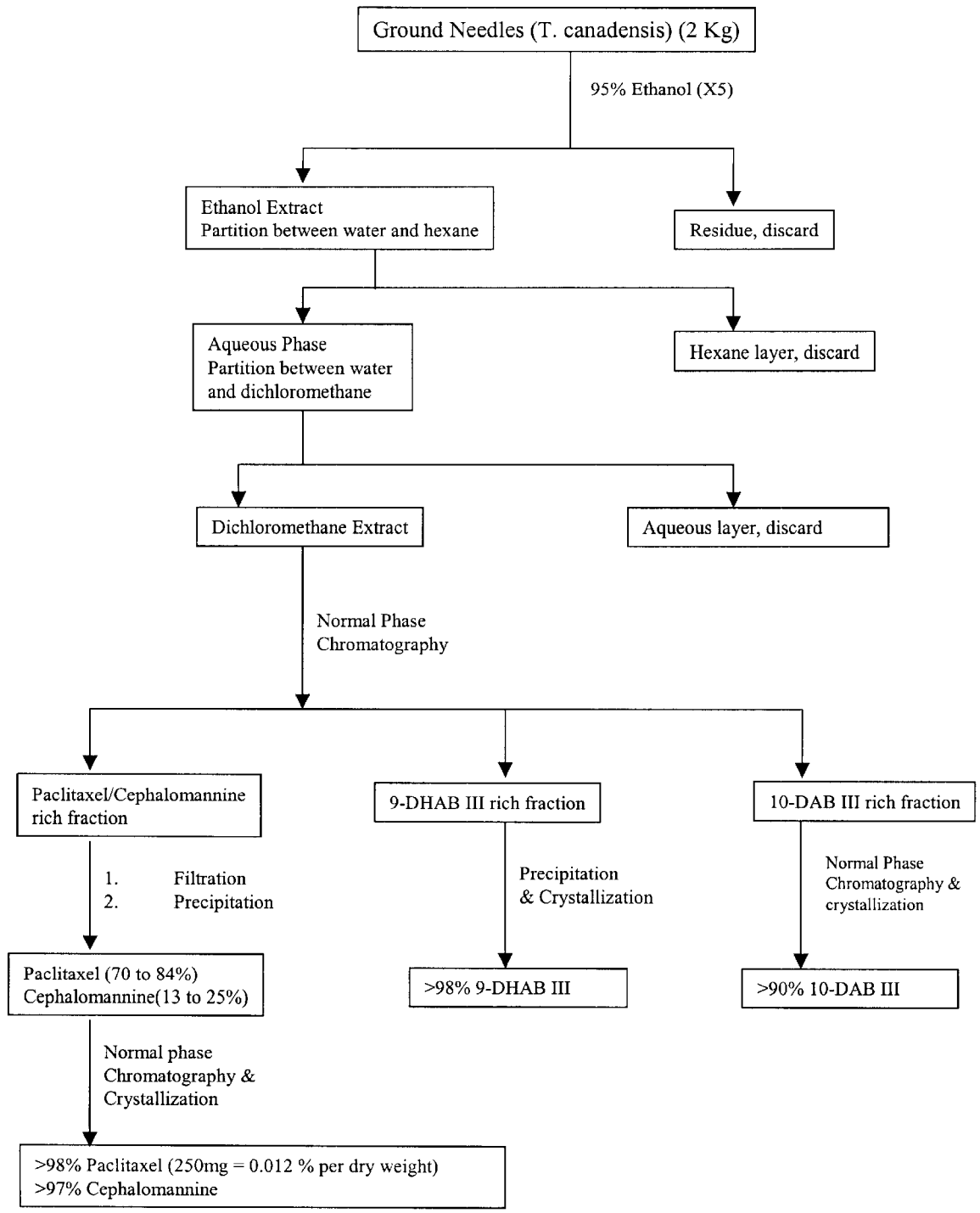
FIG. 5 is a flow diagram for the isolation and purification of paclitaxel, cephalomannine, 9-dihydro-13-acetylbaccatin III, and 10-DAB III.

In another embodiment (FIG. 5), the first residue is diluted with aqueous methanol in about 1:1 to about 1:5, (v/v) ratio of water to methanol, preferably, about 1:1. The aqueous solution is treated with hexane in about 2:1 (v/v) ratio of hexane to aqueous methanol, the resultant solution is well mixed and the layers are allowed to separate at room temperature for a sufficient period of time, i.e., at least 30 minutes. The layers are separated and the aqueous layer is extracted with hexane. The aqueous layer is then extracted with dichloromethane, chloroform, or ethyl acetate, preferably, dichloromethane in about 1:1, to 2:1, (v/v) ratio of dichloromethane to aqueous methanol. The extraction with dichloromethane can be repeated once more. The combined dichloromethane layers are washed with a dilute solution of sodium chloride of at least 2% (w/v). The volume ratio of dichloromethane extract to dilute sodium chloride solution is 1:0.5 to 1:1. The layers are allowed to separate for a sufficient period of time approximately, 30 minutes. The organic layer is dried over anhydrous drying agent such as $MgSO_4$ or $Na_2SO_4$. The organic layer is concentrated under reduced pressure to afford a second residue containing taxanes. It has been discovered that de-fating with hexane and washing with saline solution provides a cleaner second residue than the first partitioning procedure provides.

Polymeric Quenching or Scavenger Clean-up

In other embodiments, the dichloromethane layers after liquid-liquid partitions are washed with simple inexpensive weakly acidic or basic compounds, such potassium or sodium carbonate, potassium or sodium bicarbonate, triethyl amine etc., which are easily removed by an aqueous wash.

Alternatively, polymeric quenching reagents such as tris (2-ethylamino) amine polymer have been used to selectively remove undesired impurities. Accordingly, a mixture of the polymer and the crude extract (primary alcoholic extract or dichloromethane extract) in dichloromethane are stirred at ambient temperature for a sufficient period (at least 2 hours). The polymeric material is filtered off and the dichloromethane solution is concentrated under reduced pressure to afford a cleaner residue (see table 1b).

Polymeric quenching or scavenger clean-up technology is complementary to the ME and USE techniques. Because the second extracts are so much cleaner, 9-DHAB III has been precipitated from the extracts without prior chromatography. Reduced solvent and adsorbent usage in chromatography translates to reduced cost and increased efficiency in purification.

TABLE 1b

Comparative clean-up of crude dichloromethane extracts of *T. canandesis* needles extracted by USE (ethanol)

| Scavenger | Weight of crude extract (g) | Weight of crude ext. after clean-up (g) | Percent paclitaxel by hplc | Percent 9-DHAB III by hplc |
|---|---|---|---|---|
| None | 0.23 | 0.23 | <0.5 | 2.1 |
| LLP2 | 5.0 | 0.543 | 5.23 | 11.8 |
| Et$_3$N-HCl | 5.0 | 0.427 | 5.45 | 13.16 |
| K$_2$CO$_3$ | 5.0 | 0.396 | 7.88 | 23.39 |
| Polymer* | 0.5** | 0.03 | 3.9 | 7.12 |

*Tris (2-ethylamino) amine polymer
**Crude alcoholic extract

Table 1b depicts data from examples clean-up of crude extracts of *T. canandesis* needles with scavenger reagents.

Adsorptive Phase Chromatography (APC), Stage 1

Figure 3:
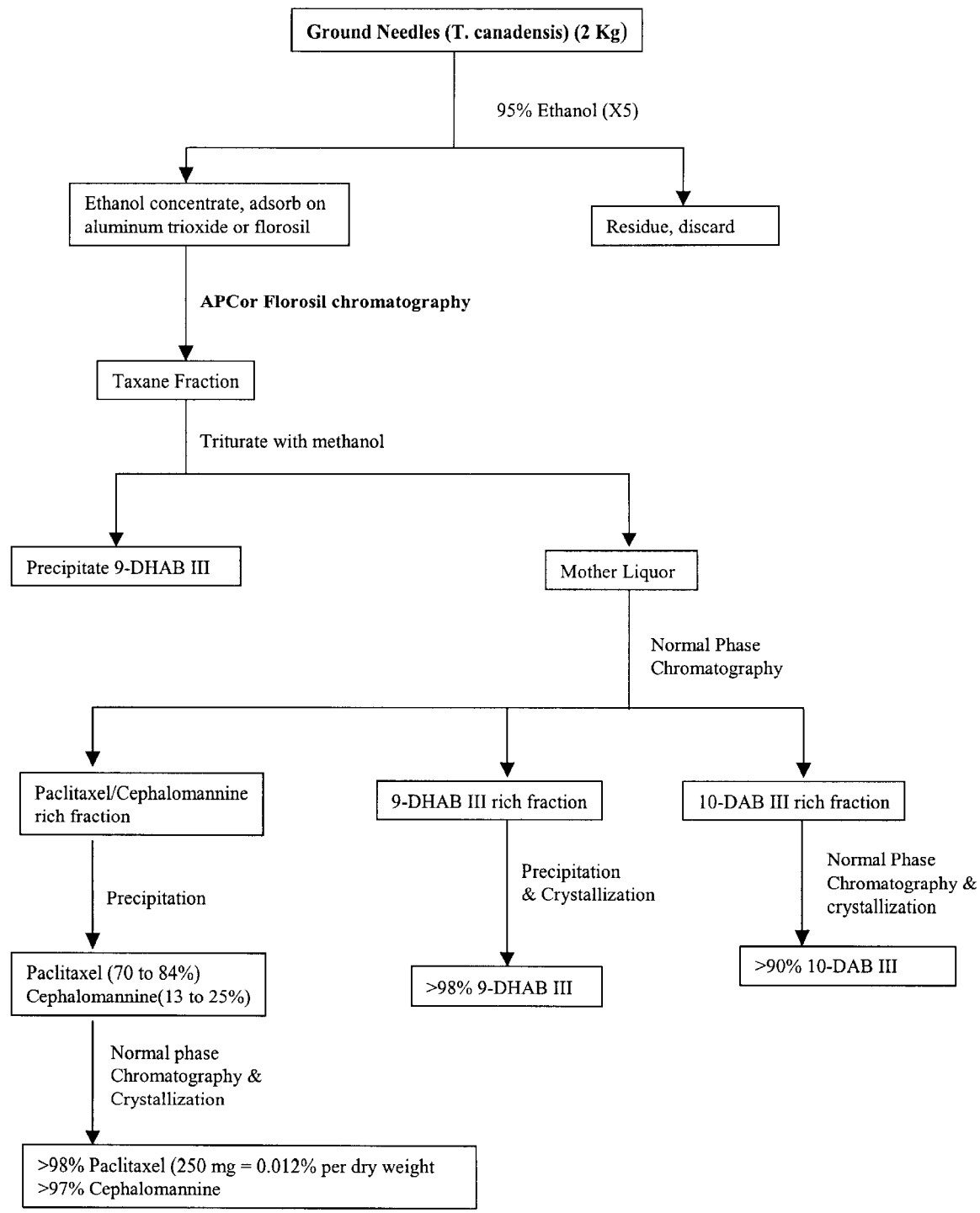
FIG. 3 is a flow diagram for the isolation and purification of paclitaxel, cephalomannine, 9-dihydro-13-acetylbaccatin III, and 10-DAB III.

In one exemplary method (See FIG. 2), the first residue is diluted with aqueous methanol in about 1:1 to about 1:5, (v/v) ratio of alcohol to water, preferably about 1:3. The aqueous layer is treated with hexane in about 2:1 (v/v) ratio of hexane to aqueous methanol. The resultant solution is well mixed and the layers are allowed to separate at room temperature for a significant period of time, i.e., at least 30 minutes. The layers are separated, and the aqueous layer is extracted once more with hexane. The aqueous layer is concentrated under reduced pressure, re-dissolved in a minimum volume of methanol, and the resultant solution is slurred on a solid support, such as silica gel or aluminum trioxide, or florosil, preferably aluminum trioxide. The ratio of sample to solid support is from about 1:4 to about 1:10, (w/w), preferably about 1:6 ratio. The mixture is air dried to a free flowing powder. In some cases, the primary alcoholic extract is adsorbed directly onto the solid support without prior de-fating with hexane. For example, when denatured alcohol is used as the extraction media, the amount of crude alcoholic extract is lower. It is advantageous in this case to adsorb the extract directly onto the aluminum trioxide without prior de-fating with hexane (see FIG. 3).

In accordance with the present invention, the aluminum trioxide adsorbed sample is applied to a glass-sintered funnel previously loaded with a small bed (approximately 1 to 2 inch) of aluminum trioxide. The size of the funnel is determined by the quantity of material to be separated. The powder on the sintered funnel is washed with dichloromethane or a mixture of dichloromethane/ethyl acetate of about 75% to 25%, which elutes less polar taxane or none taxane components. The taxanes of interest are eluted with a more polar organic solvent, a mixture of dichloromethane or ethyl acetate with a second more polar organic solvent. The second polar organic solvent can be chosen from acetone, ethyl acetate or a lower alcohol such as methanol, ethanol, or isopropyl alcohol, preferably, methanol at a concentration of about 1% to about 10%, preferably about 4% methanol in dichloromethane or ethyl acetate. The elution with the 4% methanol in dichloromethane or ethyl acetate is continued until all the 10-DAB III is eluted as indicated by tlc or hplc. The solvent is evaporated under reduced pressure to obtain a second residue containing the taxanes. This procedure advantageously eliminates hexane de-fating and the aqueous-dichloromethane partition step of earlier methods, at the same time providing a much purer pre-concentrated second residue, from which 9-DHAB III can be precipitated directly. This step also lowers the cost of subsequent chromatography steps.

In a modified matrix solid phase dispersion column chromatography (MMSPDCC), the primary extract (the crude alcoholic extract) and adsorbent (the florosil) are ground together to a free flowing powder. The weight ratio of crude extract to florosil is from about 1:2 to 1:4, preferably 1:2. The florosil adsorbed extract is applied on top of the column previously packed with florosil and equilibrated with hexane. The column is eluted with hexane/ethyl acetate mixtures from about 75% to about 25% (v/v). The advantage of using florosil is that a large proportion of undesirable biomass or plant metabolites such as chlorophyll and lignin are removed in one single step. At the same time, the desired taxanes are partitioned into distinct high yield component fractions. Paclitaxel and /or cephalomannine, 9-DHAB III, and 10-DAB III are purified from the component fractions in high yield and purity in no more than a single chromatographic step or precipitation and/ or crystallization steps.

This column is extremely efficient. It eliminates a liquid-liquid extraction step(s) and 9-Dihydro-13-acetyl baccatin III can be recovered in >95% yield. Other taxanes such as Paclitaxel can be purified by silica gel column with a sample to silica ratio of 1:50 to give Paclitaxel, Cephalomanine and 10-Deacetyl baccatin III using 1-2% methanol in dichloromethane.

This process eliminates the steps of liquid-liquid extraction, use of large quantities of chlorinated solvents, and reduction in manpower, thus translating into an overall economic savings when compared to traditional isolation methods. Florisil is high capacity adsorbent (better than silica or alumina) especially for high molecular compounds found in natural products, such as taxanes. Use of MMSP-DCC in column chromatography is unique, simplifies the loading of the compounds and thus affords a cleaner elution from the dispersion matrix.

Isolation of 9-Dihydro 13-Acetylbaccatin III

The second pre-concentrated taxane fraction (FIGS. 2 & 3) and any column fraction containing 9-DHAB III is triturated with a suitable solvent including acetone, a lower alcohol such as ethanol, methanol, or mixtures of, preferably methanol to induce precipitation. The mixture is left for a sufficient period of time, e.g., overnight at 4° C., to promote further precipitation. The precipitate is separated by vacuum filtration on a sintered funnel, washed on the sintered funnel with cold methanol, and dried under vacuum to afford 9-DHAB III (95–97%). The 9-DHAB III is re-crystallized from a suitable solvent, which includes hexane/actenoe, hexane/tetrahydrofuran, methanol, ethanol or combinations thereof. According to the present invention, denatured alcohol (95%, w/w) is the crystallization medium, from which 9-DHAB III is obtained in high yield and purity (>98%). The mother liquors are re-crystallized repeatedly to obtain more 9-DHAB III of similar purity.

Fractionation of other Taxanes, Stage 2

Purification of paclitaxel and other taxanes is accomplished by using inexpensive silica gel or neutral I aluminum trioxide, normal phase adsorbents rather than expensive bonded reverse phase adsorbents. Accordingly, the filtrate or mother liquors from the precipitation of 9-DHAB III following stage 1 adsorptive phase chromatography are concentrated under reduced pressure to provide a third taxane residue. The residue is re-dissolved in minimum acetone or dichloromethane, adsorbed on a suitable solid support such as celite or silica gel, preferably celite, and air dried to a free flowing powder. The free flowing powder is applied to glass or stainless steel columns previously loaded with silica gel in about 1:8 to about 1:40 (w/w) ratio, preferably about 1:24 (w/w) ratio of sample to adsorbent. The size of the column depends on the quantity of material to be fractionated. For example, 2 inch to 9 inches inner diameter glass or stainless steel columns have been used.

The columns are eluted in a step gradient manner with combinations of solvents such as hexane/ethyl acetate, hexane/acetone, methanol/dichloromethane, isopropyl alcohol/dichloromethane, and preferably, hexane/ethyl acetate starting from about 60% to 25%, (v/v) hexane in ethyl acetate and at a low pressure (about 5 to about 30 PSI), preferably about 10 PSI. Eluant fractions of 150 mL to 4 L each were collected at flow rate of 49 to 300 mL per minute. The fractions collected were monitored by analytical tlc and/or hplc. In this inventive process, this second stage fractionation affords four main fractions 2FA (less polar taxanes), 2FB (rich in paclitaxel/cephalomannine), 2FC (rich in 9-DHAB III), and 2FD (rich in 10-DAB III). Fraction 2FC, rich in 9-DHAB III is evaporated under reduced pressure and processed as described above to obtain additional 9-DHAB III.

Isolation of Paclitaxel and Cephalomannine, Stage 3

Fraction 2FB, a rich mixture of paclitaxel and cephalomannine is concentrated under reduced pressure to a solid residue. The residue is dissolved in a minimum amount of methanol, and water is added with stirring at room temperature until the solution appears slightly cloudy. The solution is maintained at 4° C. overnight to enhance precipitation. The crude precipitate is collected by vacuum filtration on a sintered funnel, washed on the sintered funnel with cold aqueous methanol (50% to 70% methanol in water), and dried under vacuum to afford a white to light green solid residue analyzing for paclitaxel (70–84%) and cephalomannine (13–25%), the remainder being other very minor taxane impurities.

The paclitaxel/cephalomannine solid is dissolved in a minimum volume of dichloromethane or acetone and adsorbed onto a solid support such as silica gel or celite. According to the present invention the solid support is silica gel. The ratio of sample to solid support is about 1:1 to about 1:6 (w/w), preferably about 1:3. The sample is air dried to a free flowing powder and applied to 2 inch to 9 inch inner diameter glass or stainless steel columns previously loaded with silica gel in about 1:200 to 1:350 (w/w), preferably 1:250 ratio of sample to silica gel and equilibrated with mobile phase. The mobile phase is chosen from a mixture of toluene/ethyl acetate from about 7:3 to 1:1 (v/v) or toluene/dichloromethane/ ethyl acetate from about 5:1:3 to 2:1:2 (v/v/v) or other combinations of containing toluene having similar elutropic power. It is noteworthy to mention that the toluene in the mobile phase facilitates the separation of paclitaxel from cephalomannine, presumably due to π-π interaction of the toluene with the aromatic ring of paclitaxel. The column is eluted in an isocratic manner at a low pressure (about 5 to about 10 PSI). Eluant fractions (1L) are collected at a rate of 35 mL per minute and monitored by analytical tlc and/or hplc. The fractions containing paclitaxel are pooled together and concentrated under reduced pressure to provide a solid residue, which is re-crystallized from a suitable solvent, including but not limited to hexane-acetone or aqueous methanol, to provide clinical standard paclitaxel (purity >98%).

Similarly, eluant fractions containing cephalomannine are combined, concentrated under reduced pressure to a solid residue, which is re-crystallized from a suitable solvent including but not limited to hexane-acetone or aqueous methanol to provide cephalomannine (purity: >97).

Isolation of 10-DAB III, Stage 3

10-DAB III is abundant in the needles of the European yew (*T. baccata*) and it is also found in the pacific yew (*T. brevifolia*). Modest amounts (0.002 to 0.005% per dry weight) are found in the Canadian yew (*T. canadensis*). The present invention provides the advantage that 10-DAB III can be isolated as a side stream during the isolation of paclitaxel and 9-DHAB III.

Accordingly, fraction 2FD, rich in 10-DAB III is evaporated under reduced pressure to a solid residue, which is dissolved in minimum volume of dichloromethane or acetone, adsorbed on a solid support such as silica gel or celite, preferably celite, and air dried to a free flowing powder. The powder is applied to glass columns previously loaded with silica gel and equilibrated with mobile phase. The ratio of sample to silica gel is about 1:8 to about 1:14 (w/w), preferably about 1:10. The mobile phase is chosen from a mixture of isopropyl alcohol/dichloromethane, methanol/dichloromethane or ethyl acetate/dichloromethane, preferably methanol/dichloromethane. The column is eluted in a gradient manner starting from about 2% to about 4% methanol in dichloromethane. The fractions are monitored by analytical tlc and /or hplc. The fractions containing pure 10-DAB III are pooled together and concentrated under reduced pressure to a solid residue, which is re-crystallized from acetonitrile to afford 10-DAB III (>95%).

In a second exemplary three-stage purification procedure (see FIG. 5), the crude dichloromethane extract is first fractionated on silica gel column (Stage 1). A heart-cut paclitaxel and/or cephalomannine fraction is filtered (stage 2) on neutral I aluminum trioxide. The paclitaxel and/or cephalomannine fraction obtained after filtration on neutral aluminum trioxide is precipitated with an aqueous organic solvent and then subjected to purification on silica gel column (stage 3) described above.

The advantage of this latter three-stage purification procedure is the ability for the first silica gel column (stage 1) to produce heart-cut fractions containing paclitaxel and/or cephalomannine, 9-DHAB III, and 10-DAB III in relatively high yield (>90%). Subsequent purification steps produce the desired taxanes in high yield and purity by simple precipitation/crystallization or single column chromatography step followed by precipitation and/or re-crystallization.

In a third exemplary method, paclitaxel is obtained in high yield and purity in a two-stage purification procedure. Accordingly, the crude dichloromethane extract is first fractionated by column chromatography on neutral I aluminum trioxide. The sample dissolved in minimum volume of dichloromethane is slurred on a solid support such as celite or aluminum trioxide. The weight ratio of sample to adsorbent is from about 1:1 to 1:3, preferably 1:2. The sample is air-dried under a fume hood or in a vacuum oven at low temperature not exceeding 25° C. to a free flowing powder. The free flowing powder is applied on top of a glass or stainless steel column previous loaded with neutral I aluminum trioxide. The ratio of sample to aluminum trioxide is 1:10 to 1:30, preferably 1:15. The column is eluted by gradient with dichloromethane, dichloromethane/ethyl acetate, dichloromethane/methanol or ethyl acetate/methanol mixtures. Head-cut fractions containing paclitaxel between about 2-6% (calculated yield) are obtained.

The paclitaxel fractions are subjected to a second stage chromatographic purification on silica gel previously loaded onto a glass or stainless steel column. The ratio of sample to silica gel is from about 1:14 to 1:40 (w/w), preferably 1:24. The sample is applied dissolved in minimum volume of hexane in ethyl acetate in a 1:1 (v/v) ratio. The column is eluted by gradient with hexane/ethyl acetate mixtures from about 60% to 25% hexane in ethyl acetate. Heart-cut fractions containing paclitaxel are concentrated under reduced pressure to a solid residue. The solid residue is precipitated with an aqueous organic solvent including, but not limited to acetone, methanol, denatured alcohol or acetonitrile. The precipitate is washed with cold aqueous organic solvent and re-crystallized with aqueous alcohol to clinical standard paclitaxel.

The following examples further illustrate this invention in detail but by no means limit the scope of this invention.

EXAMPLE 1

*Taxus canadensis* needles and stems were harvested in Prince Edward Island, Canada, during the month of June and dried at 70° C. for 4 hours within 24 hours of harvesting. The dried material was ground and stored in plastic bags at room temperature until processed. Dry ground material (2 Kg) was soaked in 10 L of methanol or denatured alcohol at ambient temperature. The solution was drained after a 24 hour soak period, the residue needles were re-soaked in 9 L of alcohol for 24 hours, and the solution re-drained at least two more times during a 48 hour period. The combined alcoholic extracts were concentrated under reduced pressure (15–30 mm of Hg at 40–45° C.) to a viscous residue (647 g). The residue was dissolved in methanol (3L) and water (600 mL) was added. The solution was thoroughly mixed, and hexane (7.2 L) was added. After equilibration, the layers were separated and the aqueous layer was extracted once more with hexane (7.2 L). The aqueous layer was then extracted twice with dichloromethane (2×7.2 L). The combined dichloromethane extract was dried (Anhydrous $MgSO_4$) and concentrated under reduced pressure to afford a second taxane residue (76 g).

The second taxane residue (35 g) was adsorbed onto celite (90 g), a 1:2.5 (w/w) ratio of sample to celite and air-dried to a free flowing powder for 24 hours. The free flowing powder was applied to a 2 inch internal diameter glass column previously loaded with silica gel (350 g) and equilibrated with 45% hexane in ethyl acetate. The column was eluted with hexane/ethyl acetate mixtures in a step gradient manner with 45% to 75% hexane in ethyl acetate at a pressure of 5–10 PSI. Eluant fractions of 150 mL to 200 mL each were collected at a flow rate of 49 mL/minute and analyzed by analytical tlc and hplc. The fractions rich in paclitaxel/cephalomannine, 9-DHAB III and 10-DAB III were combined separately and concentrated under reduced pressure to afford residue E1A (1.88 g), residue E1B (4.22 g), and residue E1C (2.11 g), respectively.

Residue E1B, rich in 9-DHAB III was triturated with methanol (mL) to precipitate 9-DHAB III. The resulting mixture was kept at 4° C. overnight to promote further precipitation of 9-DHAB III. The precipitate was separated by vacuum filtration on a sintered funnel, washed on the funnel with cold methanol, and dried under vacuum to afford solid 9-DHAB III (purity 96%), which was re-crystallized from denatured alcohol to afford 9-DHAB III (purity >98%).

Residue E1A (1.88 g), rich in paclitaxel/cephalomannine was triturated with methanol (5 mL) as described above to precipitate any 9-DHAB III and other undesired components. The residue (1.2 g) was dissolved in minimum volume of dichloromethane was slurred on celite (1.3 g) and the dichloromethane was evaporated under reduced pressure. The celite coated sample was applied on top of a column previously loaded with neutral I aluminum trioxide. The ratio of sample to adsorbent was 1:80. The column was eluted with methanol/dichloromethane mixtures (0.5% to 5%). Fractions containing paclitaxel/cephalomannine were combined and evaporated under reduced pressure to afford residue E1AS2 (321 mg), which analyzed for paclitaxel (78%), and cephalomanine (12%).

A portion of the crude mixture (16.5 g) analyzing for paclitaxel (81%) and cephalomannine (15.5%) was coated onto silica gel (80 g) and applied to a 4 inch inner diameter glass column previously packed with silica gel (4.6 kg) and equilibrated with a mixture of toluene: ethyl acetate: dichloromethane; 4:4:2 (v/v/v). The column was eluted with toluene: ethyl acetate: dichloromethane 4:4:2 (v/v/v) in an isocratic manner at low pressure (5 to 10 PSI) and flow rate of 35 mL/min. Eluant fraction of 1L each were collected and monitored by analytical tlc and hplc. The fractions containing paclitaxel (E1AS3) and cephalomannine (E1BS3) were combined separately and concentrated under reduced pressure to afford 12.5 gm and 2.2 gm of paclitaxel and cephalomannine, respectively.

Fraction E1AS3 was re-crystallized with aqueous methanol to afford paclitaxel, 1 (10.5 g; purity: 98%; yield:0.015%). Similarly fraction E1BS3 was re-crystallized from aqueous methanol to afford cephalomannine, 3 (1.5 g; purity: 97%; yield: 0.002%).

Residue E1C, rich in 10-DAB III was dissolved in minimum volume of acetone, adsorbed onto celite, and the mixture is air-dried to a free flowing powder. The powder was applied to a 1" diameter glass column previously loaded with silica gel and equilibrated with 2% methanol in dichloromethane. The column was eluted at low pressure (5 to 10 PSI) with methanol in dichloromethane in a gradient manner starting with 2% and ending with 4%. Eluant fractions of 250 mL were collected at a flow rate of 50 mL/min. The fractions were monitored by analytical tlc and hplc, and fractions containing 10-DAB III were combined, concentrated under reduced pressure to a solid residue, which was re-crystallized from acetonitrile to afford 10-DAB III.

EXAMPLE 2

Dried ground needles and stems (2 Kg) of *T. canadensis* were extracted with denatured ethanol according to the procedure of example 1. The first concentrated residue (658 g) was de-fated by partition between aqueous ethanol (3L) and hexane (2×6L) according to the method of example 1. The aqueous ethanol layer was concentrated to two-thirds its volume, slurred on aluminum trioxide (3.576 g), and air-dried to a free flowing powder.

An aluminum trioxide coated sample (1.1 kg) was applied to a 2L (v) and 5 inches inner diameter sintered funnel previously loaded with a layer (200 g) of Neutral I aluminum trioxide. The sample was washed by vacuum filtration with dichloromethane (12 L) to remove none polar metabolites. The taxanes were eluted with 4% methanol in dichloromethane (16 L) and the eluant was concentrated under reduced pressure to afford a second residue (10 g).

The second residue was triturated with methanol (50 mL) and left at 4° C. overnight to facilitate precipitation of 9-DHAB III. The 9-DHAB III was separated by vacuum filtration on a sintered funnel, and washed on the sintered funnel with cold methanol to afford 9-DHAB III (140 mg). The 9-DHAB III was recrystallized from denatured alcohol to afford 9-DHAB III (>98%). The filtrate or mother liquors were processed according to example 1 to obtain paclitaxel, cephalomannine and 10-DHAB III.

EXAMPLE 3

Dry ground needles (50 Kg) were soaked in 250 L of methanol in a 300 L stainless steel container at ambient temperature. After 24 hours soak period, the solution was drained (approx. 150 L). The residue needles were contacted with fresh methanol (150 L), soaked for a second 24 hours period, and subsequently drained. The extraction procedure was repeated for the third time to yield approximately 450 L of combined crude alcoholic extract. The combined alcoholic extracts were concentrated under reduced pressure and temperature not exceeding 40° C. to 30 L of residue. The residue was diluted with water (6 L) and hexane (72 L) was added. The mixture was agitated with a mechanical agitator for 15 minutes. The layers were allowed to separate for at least 2 hours and the aqueous layer was de-fated once more with hexane (72 L). The aqueous layer was diluted with water (24 L), dichloromethane (120 L) was added, and the mixture was agitated with a mechanical agitator for 15 minutes. The layers were allowed to separate for at least 2 hours and the aqueous layer was treated once more with dichloromethane (60 L). The mixture was agitated for 15 minutes and the layers were allowed to separate for at least 2 hours. The combined dichloromethane layer was dried over anhydrous MgSO4 (3 Kg) and concentrated under reduced pressure at temperature not exceeding 25° C. to afford a second residue (approx. 1.7 Kg). In similar extraction protocols where the combined dichloromethane extracts were washed with 2% saline solution prior to drying over anhydrous $MgSO_4$, 1.4 to 1.5 Kg of a second residue was obtained.

EXAMPLE 3A
Three Stage Purification Procedure

A six inches internal diameter stainless steel column was packed with silica gel (10 Kg) and equilibrated with 50% hexane in ethyl acetate. The crude dichloromethane extract (322 g) dissolved in minimum volume of dichloromethane was slurred on celite (586 g). The dichloromethane was removed by air-drying, and the celite adsorbed sample was applied on top of the silica gel column. The column was eluted with ethyl acetate/hexane mixtures (50% to 70%) at a flow rate of 210 mL to 260 mL per minute. Eluant fractions of 1 L each were collected and monitored by tlc and/or hplc. The fractions rich in paclitaxel, paclitaxel/cephalomannine, 9-DHAB III, and 10-DAB III were combined separately and concentrated under reduced pressure to afford residue E3Aa (4.11 g), residue E3Ab (6.70 g), residue E3Ac (33.11 g), and residue E3Ad (22.82 g), respectively.

Residue E3Ac (33.22 g), rich in 9-DHAB III was triturated with methanol (100 mL) to precipitate 9-DHAB III. The resulting mixture was kept at 4° C. overnight to promote further precipitation of 9-DAB III. The 9-DHAB III precipitate was separated by vacuum filtration on a sintered funnel, washed on the funnel with cold methanol, and dried under vacuum to afford white solid 9-DHAB III (6 g, purity >95%).

The paclitaxel containing residues E3Aa (4.11 g) and E3Ab (6.70 g) were each separately subjected to filtration on a column of neutral I aluminum trioxide. The weight ratio of sample to aluminum trioxide was 1:40. The sample was applied on top of the column as a solution in minimum volume of dichloromethane and the column was eluted with methanol/dichloromethane mixtures (0.5% to 5%). Fractions containing paclitaxel were combined, concentrated under reduced pressure, and precipitated with aqueous alcohol to afford E3AaS2 paclitaxel (1.0 g, purity >95%) and E3AbS2 paclitaxel/cephalomannine mixture (1.3 g).

Sample E3AbS2 (0.93 g) analyzed for 64% (paclitaxel) and 29% (cephalomannine) was re-chromatographed on silica gel. The ratio of sample to silica gel was 1 to 240. The column was eluted isocratically with toluene in ethyl acetate in a ratio of 3:2 (v/v). The fractions containing paclitaxel and cephalomannine were combined and evaporated separately to afford E3AaS3, paclitaxel (0.42 g) and E3AaS3, cephalomannine (0.21 g). The paclitaxel was re-crystallized from aqueous methanol to afford clinical standard paclitaxel 1 (0.3 g, purity >99%).

EXAMPLE 3B
Two Stage Purification Procedure

A six inches internal diameter glass column was packed with neutral I aluminum trioxide (15 Kg) and equilibrated with dichloromethane. A sample (0.8 Kg) of the second residue (crude dichloromethane extract) was dissolved in dichloromethane (700 mL) and applied on top of the column. The column was eluted under gravity at a flow rate of 125 to 150 mL per minute and gradient elution with methanol/dichloromethane mixtures starting from pure dichloromethane to between 0.5% and 10% methanol in dichloromethane. Eluant fractions of 1 L to 1.5 L were collected and monitored by tlc and/or hplc. The fractions containing 9-DHAB III (residue E3Ba), paclitaxel/cephalomannine (residue E3Bb), and 10-DAB III (residue E3Bc) were combined and evaporated separately. The fractions containing 9-DHAB III were triturated with methanol as described earlier to afford 9-DHAB III (9 g, purity >95%).

Residue E3Bb (74.8 g), a paclitaxel/cephalomannine rich fraction was dissolved in minimum volume of dichloromethane and slurred on celite (115 g). The dichloromethane was evaporated under reduced pressure, and the celite adsorbed sample was applied on top of a 4 inches internal diameter column previously loaded with silica gel (3 Kg) and equilibrated with 50% hexane in ethyl acetate. The column was eluted isocratically with 45% hexane in ethyl acetate to afford fractions containing mainly paclitaxel (4.4 g, purity >84%), paclitaxel/cephalomanine (0.8 g), and cephalomanine/9-DHAB III (6.3 g).

The paclitaxel fraction (4.4 g) was precipitated and then re-crystallized from aqueous methanol to afford paclitaxel (2.7 g, purity 96 to 98%).

EXAMPLE 3C
Two Stage Purification Procedure

A six inches internal diameter glass column was packed with neutral I aluminum trioxide (11.8 Kg) and equilibrated with dichloromethane. The crude dichloromethane extract (520 g) dissolved in minimum volume of dichloromethane was slurred on celite (1 kg). The dichloromethane was removed by air-drying at ambient temperature and the celite-coated sample was applied on top of the column. The column was eluted under gravity at a flow rate of approximately 200 mL per minute with ethyl acetate/dichloromethane (50%) and methanol/ethyl acetate mixtures from about 1% to about 10 %. Eluant fractions of 1 L to 1.5 L were collected and monitored by tic and/or hplc. The fractions containing 9-DHAB III (residue E3Ca), paclitaxel/cephalomannine (residue E3Cb), and 10-DAB III (residue E3Cc) were combined and evaporated separately. The fractions containing 9-DHAB III were triturated with methanol as described earlier to afford 9-DHAB III (6 g, purity >95%).

Residue E3Cb was fractionated by column chromatography using the same procedure described for example-3B to afford paclitaxel and cephalomannine.

EXAMPLE 4

Ground dry needles (2×500 g) in a 2 L Pyrex beaker were contacted with 1 L methanol. The mixture was agitated with a mechanical stirrer for 2 minutes and then exposed to microwave radiation for 20 seconds. The agitation for 2 minutes and exposure to microwave radiation was repeated once more and the solution was drained. The residue solids were contacted with fresh 1 L of methanol and the ME procedure was repeated. The combined alcoholic extracts were evaporated under reduced pressure and temperature not exceeding 30° C. to afford a total of 318 g of solvent free primary extract. A sample of the crude primary extract (25.51 g) and florosil (50.24 g) were ground together in a Motor and Persil to a free flowing powder. The free flowing powder was loaded on top of a florosil column previous loaded with florosil (375 g) and equilibrated with hexane. The column was eluted with hexane in ethyl acetate mixtures (70% to 40%). Fractions containing none taxanes, 9-DHAB III, paclitaxel/cephalomannine, and 10-DAB III were combined and evaporated separately to afford E4A (1.291 g), E4B (0.157 g), E4C (0.168 g), E4D (0.032 g), respectively.

Therefore, about 93% of biomass was retained on florosil in a single chromatographic step devoid of liquid-liquid partition steps and use of excessive quantity of toxic chlorinated solvent.

One skilled in the art will appreciate further features and advantages of the invention based on the above-described embodiments. Accordingly, the invention is not to be limited by what has been particularly shown and described, except as indicated by the appended claims. All publications and references cited herein, including those in the background, are expressly incorporated herein by reference in their entirety.

What is claimed is:

1. A method for preparing at least one purified taxane, comprising the steps of:
   a) providing a sufficient quantity of biomaterial derived from *T. canadensis;*
   b) treating the biomaterial with a sufficient quantity of a lower molecular weight alcohol to provide a crude alcoholic extract;
   c) concentrating the alcoholic extract to provide a concentrate;
   d) adsorbing the concentrate onto a solid support;
   e) drying the extract on the solid support;
   f) removing less polar metabolites from the support with a non-polar solvent; and
   g) removing polar taxanes from the support with a polar organic solvent to afford one or more taxanes.

2. The method of claim 1, further comprising the step of triturating the taxanes from step g), thereby causing a single taxane to precipitate from solution.

3. The method of claim 2, wherein the single taxane is 9-DHAB III.

4. The method of claim 1, wherein the biomaterial is fresh or dried leaves and stems.

5. The method of claim 1, wherein the non-polar solvent is dichloromethane or a mixture of dichloromethane and ethyl acetate.

6. The method of claim 1, wherein the polar solvent is selected from the group consisting of acetone, tetrahydrofuran, methanol, ethanol, isopropyl alcohol and combinations thereof.

7. The method of claim 1, further comprising the steps of:
   a) collecting the mother liquors from step g);
   b) adsorbing the mother liquors onto a normal phase adsorbent; and
   c) separating components from the adsorbent.

8. The method of claim 1, further comprising the steps of:
   a) dissolving the concentrate from step c) into a suitable solvent to form a concentrated solution; and
   b) treating the concentrated solution with a scavenging reagent, suitable for removal of impurities.

9. The method of claim 8, wherein the scavenging reagent is selected from the group consisting of tris(2-ethylamino) amine polymer, metal carbonates and tertiary amines.

10. The method of claim 1, wherein the solid support is aluminum trioxide.

11. A method of extraction of taxanes from a biomaterial, comprising the steps of:
    a) treating a taxane containing biomaterial with a non-polar solvent;
    b) exposing the non-polar solvent taxane mixture to microwave radiation;
    c) removing the non-polar solvent from the taxane containing biomaterial;
    d) treating the taxane containing biomaterial from step c) with a polar solvent;
    e) exposing the polar solvent taxane mixture to microwave radiation, resulting in a polar extract; and
    f) separating the polar extract from the remaining taxane biomaterial.

12. The method of claim 11, further comprising the step of contacting the polar extract with an adsorbent suitable for chromatography.

13. The method of claim 11, wherein the non-polar solvent is hexane.

14. The method of claim 11, wherein the polar solvent is a low molecular weight alcohol.

15. The method of claim 14, wherein the low molecular weight alcohol is selected from the group consisting of ethanol, methanol and isopropanol.

16. A method of extraction of taxanes from a biomaterial, comprising the steps of:
    a) combining a mixture of taxane containing biomaterial and an adsorbent;
    b) add the mixture to a column suitable for elution; and
    c) eluting the mixture with a non-polar solvent and a polar solvent combination, thereby providing enriched fractions of Paclitaxel, 9-DHAB III or 10-DAB III.

17. The method of claim 16, wherein the adsorbent is florosil.

18. The method of claim 16, wherein the non-polar solvent is hexane.

19. The method of claim 16, wherein the polar solvent is ethyl acetate.

20. The method of claim 16, wherein the solvent combination is a gradient of non-polar and polar solvents, the solvent gradient beginning at 75% non-polar solvent (v/v) to 25% (v/v).

21. A method of extraction of taxanes from a biomaterial, comprising the steps of:
   a) treating a taxane containing biomaterial with a non-polar solvent;
   b) exposing the non-polar solvent taxane mixture to ultrasonic radiation;
   c) removing the non-polar solvent from the taxane containing biomaterial;
   d) treating the taxane containing biomaterial from step c) with a polar solvent;
   e) exposing the polar solvent taxane mixture to ultrasonic radiation, resulting in a polar extract; and
   f) separating the polar extract from the remaining taxane biomaterial.

22. The method of claim 21, further comprising the step of contacting the polar extract with an adsorbent suitable for chromatography.

23. The method of claim 21, wherein the non-polar solvent is hexane.

24. The method of claim 21, wherein the polar solvent is a low molecular weight alcohol.

25. The method of claim 24, wherein the low molecular weight alcohol is selected from the group consisting of ethanol, methanol and isopropanol.

* * * * *